United States Patent [19]

Flynn

[11] 4,283,447

[45] Aug. 11, 1981

[54] RADIOPAQUE POLYURETHANE RESIN COMPOSITIONS

[76] Inventor: Vincent J. Flynn, 130 New Rd., Apt. D10, Parsippany, N.J. 07054

[21] Appl. No.: 108,393

[22] Filed: Dec. 28, 1979

Related U.S. Application Data

[60] Division of Ser. No. 40,278, May 18, 1979, Pat. No. 4,250,072, which is a continuation-in-part of Ser. No. 862,773, Dec. 21, 1977, abandoned, which is a continuation of Ser. No. 712,189, Aug. 6, 1976, abandoned.

[51] Int. Cl.$^3$ ............................ F16L 9/00; F16L 11/00
[52] U.S. Cl. ...................................... 428/36; 138/118; 138/177
[58] Field of Search ...................... 260/31.2 N, 31.4 R; 138/177, 118; 428/36

[56] References Cited

U.S. PATENT DOCUMENTS

| | | | |
|---|---|---|---|
| 3,356,650 | 12/1967 | McElroy | 260/31.4 R |
| 3,361,700 | 1/1968 | Archer et al. | 260/31.4 R |
| 3,489,723 | 1/1970 | Kraft | 260/31.2 N |
| 3,645,955 | 2/1972 | Flynn | 260/31.4 R |
| 3,752,617 | 8/1973 | Burlis et al. | 425/131 |

OTHER PUBLICATIONS

Encyclopedia of Polymer Science & Technology, vol. 11, pp. 506–563, No. 4, Interscience Publ. (1969).

*Primary Examiner*—Harry Wong, Jr.
*Attorney, Agent, or Firm*—Morgan, Finnegan, Pine, Foley & Lee

[57] ABSTRACT

Radiopaque compositions are provided by formulating polyurethane resins, alone, or combined with vinyl resins, with alkyl or alkoxyalkyl 2,5-diiodobenzoates, 2,3,4,6-tetraiodobenzoates or mixtures thereof. The compositions are useful in the manufacture of X-ray opaque medical devices, particularly medical surgical tubing. Surgical tubing with excellent plastic memory is provided, well adapted to forming flares and curved tips necessary for selective renal and celial arteriography. Multi-wall and co-tapered multiwall tubing constructions are also disclosed.

6 Claims, 6 Drawing Figures

RADIOPAQUE POLYURETHANE RESIN COMPOSITIONS

This application is a division of Ser. No. 40,278, filed May 18, 1979, now U.S. Pat. No. 4,250,072 which in turn is a continuation-in-part of copending application Ser. No. 862,773, filed Dec. 21, 1977, now abandoned, which in turn is a continuation of application Ser. No. 712,189, filed Aug. 6, 1976, now abandoned.

This invention relates to novel radiopaque resin compositions and shaped articles prepared therefrom. More particularly, the invention pertains to compositions of polyurethane resins, alone, or in combination with vinyl resins, and polyiodobenzoic acid esters and their use in medical-surgical devices.

BACKGROUND OF THE INVENTION

Archer and Flynn, U.S. Pat. No. 3,361,700, discloses that a family of alkoxyalkyl esters of diiodobenzoic acid are radiopaque and suitable to plasticize vinyl resins into a form useful to manufacture tubings for catheters and similar products. Flynn, U.S. Pat. No. 3,645,955 discloses that di- and tetraiodoesters used alone or in combination with the alkoxyalkyl diiodoesters are superior for this purpose because they show less tendency to exude and lower concentrations provide a better balance between flexibility and stiffness. In the copending application of Flynn, Ser. No. 862,773, there are described certain multi-wall tubing constructions, with a passing mention of polyurethane as a material of construction, but no suggestion is made that this be combined with any radiopacifier, especially the iodoesters mentioned above. Burlis et al, U.S. Pat. No. 3,752,617 disclose methods for making multiwall tubing, co-tapered along its length, but use plastics other than polyurethane, and make no mention of any additives, specifically by name, to produce different X-ray sensitive characteristics. The foregoing patents and application are all incorporated herein by reference.

While the iodoester opacified vinyl resin compositions are quite suitable for the production of tubing of simple types useful for intubation sets and catheter needles, they are not completely satisfactory for production of shaped devices. For example, if flared, or if formed into curved tips, the shapes tend to revert to straight tubing—a so-called loss of plastic memory effect. It has now been found that if the vinyl resin is replaced partially or completely by a thermoplastic polyurethane, the iodoester radiopacified compositions are amenable to the induction of complex shapes—and they'll stay that way. Such tubings provide catheters eminently suitable for selective renal arteriography and for celial arteriography, and also for the manufacture of pig-tail catheters. Surprisingly, the iodoesters do not show the same tendency to overplasticize the urethane esters as they do the vinyl esters, and, moreover, there is lesser need to use a radioparent plasticizer with urethanes and, in fact, it is preferred to omit a radioparent plasticizer completely. As will be shown, the new compositions lend themselves well to the formation of highly advantageous multi-wall tubing constructions. In one feature of the invention, a thin, inner core of iodoester-radiopacified polyurethane and a thicker outer core of plasticized vinyl resin eliminates extraction problems with fluids passing through the core. In another feature, an inner core of nylon or polypropylene will provide an outer jacket of iodoester radiopacified urethane or urethane-vinyl with stiffness, but much less tendency to kink in a multiwall construction; and such tubes are also easily manufactured in a co-tapered wall thickness construction in which the variations in twisting resistance provide enhanced ease of insertion through torturous body passages.

In summary, optically clear radiopaque formulations based on thermoplastic polyurethane (TPU) according to this invention have the following distinct advantages over vinyl (PVC)-based compositions of the prior art:

(i) ease and flexibility in formulation and processing: In contrast to PVC formulations, TPU does not require a primary plasticizer or heat stabilizer. PVC-based systems, in general, are temperature and shear sensitive, and consequently, the melt processing range is rather limited.

(ii) potentially less toxic: PVC is more susceptible to thermal/shear induced degradation. In plasticized PVC formulations, both the plasticizer and the residual monomer are subject to migration and extraction phenomena. (The newer grades of PVC, admittedly, contain insignificant quantity of residual monomer). In recent years, PVC has come under increased public scrutiny and criticism.

(iii) physical and functional properties: TPU can be formulated to obtain a much broader range of physical properties, if desired. Distinct advantages of TPU formulations will be in higher tensile strength, elongation and excellent abrasion resistance and tear strength, and especially in retention of plastic memory.

(iv) better blood compatibility: In many tests, the thrombo-resistance of TPU has been shown to be superior to PVC.

(v) better ability to accept heparinization.

BRIEF DESCRIPTION OF THE DRAWINGS

The invention will be better understood by reference to the accompanying drawings in which.

DESCRIPTION OF THE INVENTION

Figure 1:
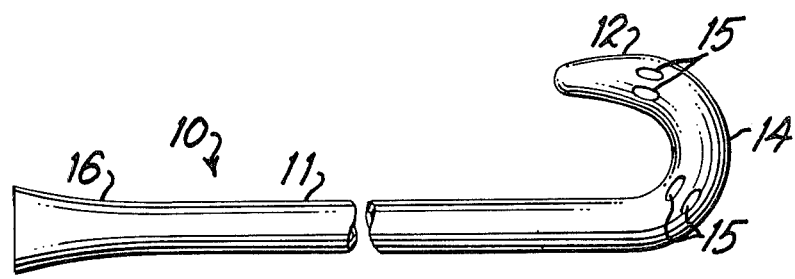
FIG. 1 is a longitudinal view of a catheter made from one form of the tubing made in accordance with the present invention and wherein, for illustrative purposes, the distal end is tapered and shaped to form a "J" tip, and the proximal end is flared.

In accordance with the present invention, there are provided radiopaque composition comprising (a) a resin which includes from 100 to 33 parts by weight of a thermoplastic polyurethane and from 0 to 67 parts of a polymer or copolymer of a halogenated vinyl monomer; and (b) a radiopacifier therefor consisting of a diiodobenzoate or a tetraiodobenzoate of the formula

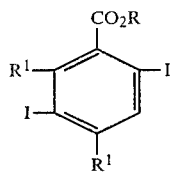

wherein $R^1$ is hydrogen or iodo, R is alkyl or alkoxyalkyl and a mixture of said compounds, said radiopacifier (b) comprising 10 to 40 parts by weight per 100 parts by weight of (a) and (b).

Preferably each $R^1$ is iodo and R is (lower)alkyl or (lower)alkoxy (lower)alkyl. The most preferred radiopacifiers are n-butyl 2,3,4,6-tetraiodobenzoate, 2-ethoxyethyl 2,5-diiodobenzoate, or a mixture thereof.

The thermoplastic polyurethanes are known to those skilled in this art. They are described in the Encyclopedia of Polymer Science and Technology, Vol. 11, pages 506–563, New York, Interscience Publishers, 1969, and especially on page 549. They are also commercially available from a number of suppliers, such as Hooker, as Rucothenes, especially 3713, and from Upjohn, as Pellethene 75D, from Mobay, as Texin, and from Uniroyal, as Roylar.

Suitable vinyl resins are described in the abovementioned U.S. Pat. No. 3,645,955. They are available from a number of sources, such as Escambia, Nos. 3225, 3250 and 3255; Diamond No. 450 and No. 500; Borden, 106PM and Dow Chemical Co., 100-4.

The radiopacifier compounds (b) can be made by procedures fully described in the above mentioned U.S. Pat. Nos. 3,645,955 and 3,361,700. In general, a 2,3,4,6-tetraiodobenzoyl halide or 2,5-diiodobenzoyl halide will be treated with an alkanol or alkoxyalkanol at ordinary temperatures, preferably in the presence of an acid acceptor. Alternatively, the free acid can be reacted with a sodium alkoxide or alkoxyalkoxide. The product can be recovered and purified in a known way e.g., distillation When used in the appended claims, the term "alkyl" contemplates straight and branched chain radicals of from 1 to 30 carbon atoms, and the term "(lower)alkyl" contemplates such groups of from 1 to 6 carbon atoms.

The term "radioparent" plasticizer means a conventional plasticizer, for example, a dialkyl ester of aromatic or aliphatic polybasic acids, e.g., dioctyl adipate, which is commercially available from Rohm & Haas Co., as Monoplex DIOA. Also contemplated are epoxy plasticizers, such as Swift & Co.'s Epoxol 9-5. The term "heat stabilizer for said vinyl resin" embraces metallic salts, based on tin, calcium, zinc and the like. A suitable commercial heat stabilizer is based on calcium and zinc, available from Advance Division of Carlisle Chemical Works. As CZ-11C.

The formulations will be aided in some cases by the inclusion of lubricants such as metallic stearate, stearic acid, paraffin wax, mineral oil, etc., in conventional amounts. See U.S. Pat. No. 3,645,955, incorporated herein to minimize unnecessarily detailed description.

The compositions are prepared and converted into useful products by techniques well known to those skilled in the art.

In one manner of proceeding, the fluid ingredients, e.g., radiopaque compound(s) if liquid, are blended with the powdered solids, e.g., thermoplastic polyurethane resin and, optional, vinyl resin, stabilizers and plasticizers and then fused and mixed under pressure, e.g., in a Banbury-type mixer and discharged. Conventional 2-roll compounding techniques can also be used. The composition is cooled and granulated.

If extrusions are to be made, the granulated composition can be fed to a conventional machine, for example, a 30 millimeter Reifenhauser-type single screw extruder operated at suitable temperature, e.g., 280°–330° F. and the tubing or other shapes formed at a suitable rate, e.g., 7,000-10,000 feet per hour and cut automatically to length.

As is pointed out above, the compositions of this invention can be used for many various and diverse purposes, e.g., protective sheeting, surgeon's gloves, intubation sets, heart catheters, stomach tubes, nasal tubes, thoracic catheters and the like. The following examples primarily illustrate the use of these compositions in the form of single and multiple wall surgical tubing. However, from the foregoing description and the following examples and by reference to other well known teachings, the methods and modes by which the plasticized radiopaque urethane resin compositions of this invention can be formed into various other articles will be readily apparent to those skilled in the art.

The medical grade radiopaque tubing prepared as described in the following examples is non-toxic, non-reactive to tissue and may be sterilized by gas or cold sterilization solutions. The tubing is generally dispensed as such and the surgeon or trained technician will form it into catheters for roentgenography. For maximum convenience, the tubing can also be preformed into articles and dispensed, e.g., as sterile disposable intravenous catheters.

By way of illustration, catheters according to this invention will be fabricated from the medical-surgical tubing of the following examples by operations comprising tip forming, tip finishing, shaping, side hole forming, and flaring. Before use they will be sterilized.

Those skilled in the art will prepare a variety of tip shapes. For internal mammary and axillary artery branches a three-quarter loop is formed in the distal end. For precutaneous arteriography and cerebral arteriography via femoral, a 45°–60° smooth bend will be formed in the distal end. Selective renal arteriography and celiac arteriography requires a onehalf loop. Hepatic venography uses about a seven-eighths loop. For trans-septal left-heart catheterization via the femoral vein, a three-quarter loop, like that above-described for mammary branches, but larger, is formed. On the other hand, abdominal aortography via brachial artery uses a rather large, one-third closed loop and thoracic aortography via the femoral artery uses the same shape but bigger. For lumbar aortography via the femoral artery the tip is straight out. For coronary arteriography, the end of the catheter is looped.

The heavier-walled tubing is formed into such typical shapes by inserting a forming wire within the tubing and heating in a tiny flame until visibly softened. By pulling from both ends the tubing is drawn to the wire and forms a uniform lumen around it. The tip is formed by cutting, e.g., with a razor blade, at the drawn diameter and is smoothly rounded in the flame. Next a precurved wire is inserted into the tube which is then immersed in hot water until the tubing softens. Quenching in cold water will cause the catheter to conform to the curve of the forming wire. Side hole or eye punching is accomplished by rotating a sharpened hole punch cannula under slight pressure. The holes should be large enough to expel contrast media without excess build up of injection pressures but should be no larger than ⅔ of the internal diameter of the tubing. The catheter is cut to the preselected length and flared. Heating in a small flame and rotating on a flaring tool produces a flare of the desired size. The catheter can be bonded at the flare, e.g., with epoxy cement, to a suitable hub. On the other hand, an adapter can be used to screw the catheter to a Luer-Lok stopcock, or the like.

DESCRIPTION OF THE PREFERRED EMBODIMENTS

The following non-limiting examples illustrate the present invention.

EXAMPLES 1-5

| Composition (parts by weight) | Example | | | | |
|---|---|---|---|---|---|
| | 1 | 2 | 3 | 4 | 5 |
| Resin, thermoplastic polyurethane, Hooker Rucothane 3713 | 1800 | 36.23 | 67.47 | 66.66 | — |
| Resin, thermoplastic polyurethane Roylar 65N Uniroyal | — | 36.23 | — | — | 66.6 |
| n-Butyl 2,3,4,6-tetraiodobenzoate | 500 | 27.52 | 32.53 | 33.33 | 33.33 |

Figure 2:
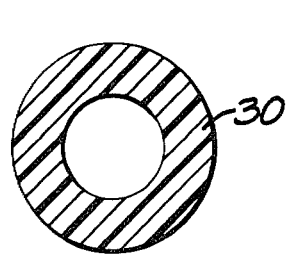
FIG. 2 is an enlarged cross-sectional view of radiopaque tubing according to this invention.

The compositions are mixed in a Banbury mixer for 4 minutes at 345° F. and for 2 minutes at 310° F., discharged, and granulated through a ⅛ in. screen. The granulated products are extruded in a 30 mm. Reifenhauser screw extruder at 310°-330° F. into medical-surgical single wall tubing of the type shown in FIG. 2, 0.065 O.D.×0.044 I.D.—wall 0.0105", having properties eminently suitable for use as intubation sets and in catheter needles.

EXAMPLES 6-10

The procedure of Example 1 is repeated, partially or completely replacing the 2,3,4,6-tetraiodo compound with a 2,5-diiodoester.

| Composition (parts by weight) | Example | | | | |
|---|---|---|---|---|---|
| | 6 | 7 | 8 | 9 | 10 |
| Resin, thermoplastic polyurethane Royalr 65N, Uniroyal | 66.66 | 69.02 | 67.8 | — | — |
| Resin, thermoplastic polyurethane Rucothene 3713 | — | — | — | 66.66 | 66.66 |
| n-Butyl 2,3,4,6-tetraiodobenzyl | — | 15.70 | 26.5 | — | 16.67 |
| 2-Ethoxyethyl 2,5-diiodobenzoate | 33.33 | 15.70 | 7.5 | 33.33 | 16.67 |

Thin wall tubings extruded from these compositions are clear and useful for making catheters.

EXAMPLES 11-15

The procedure of Example 1 is repeated, effecting partial replacement of the polyurethane with vinyl resin in the following formulations

| Composition (parts by weight) | Example | | | | |
|---|---|---|---|---|---|
| | 11 | 12 | 13 | 14 | 15 |
| Resin, thermoplastic polyurethane Rucothene 3713 | — | 46.25 | 48.12 | 33.75 | 23.12 |
| Resin, thermoplastic poly-urethane Rucothene 363 | 25.00 | — | — | — | — |
| Resin polyvinyl chloride, Goodyear BK 80 | 43.73 | 21.86 | 27.18 | 32.50 | 43.23 |
| n-Butyl 2,3,4,6-tetraiodobenzoate | 12.36 | 22.43 | 11.21 | 16.25 | 11.21 |
| 2-ethoxyethyl 2,5-diodobenzoate | 12.99 | 6.49 | 10.74 | 15.00 | 18.24 |
| Epoxy plasticizer, Epoxol 9-5 | 5.12 | 2.56 | 2.28 | 2.00 | 3.28 |
| Calcium zinc stabilizer, CZ11C | 0.78 | 0.39 | 0.45 | 0.5 | 0.69 |

Flexible tubings having utility in intubation sets are obtained.

EXAMPLE 16

The procedure of Example 1 is repeated, but the extruded tubing has an outer diameter of 0.098 inch and an inside diameter of 0.054 inch. This is formed into a finished catheter as illustrated in FIG. 1. Tubing 10 tapers down to a main body section 11 of substantially uniform cross-section to a curved J-shaped tip 12 as its distal end 14. One or more eyes or openings 15 are also provided in the distal end 14 for passages of fluids through the tubing 10. The proximal end of tubing 10 flares outwardly for receiving various equipment such as syringes for injecting fluids into the patient. The tapering and curvature of the tip, the flaring of the eyes and the flaring of the end are all effected by heated tools which utilize the thermoplastic properties of the extruded tubing. This single wall tubing has a cross-section as in FIG. 2 where reference numeral 30 illustrates the radiopaque composition of this invention.

Unlike catheters made from wholly vinyl resins, the catheter of this example readily resumes its shape after stretching and deforming.

EXAMPLE 17

A double wall radiopaque medical-surgical tubing is extruded in the temperature range of 310° F. to 330° F. in a conventional manner using conventional extrusion equipment having a biorifice tubular die for coextrusion of an inner core and an outer shell bonded to said inner tube. The tubing has an outer diameter of 0.098 inch and an inner diameter of 0.054 inch, and the inner tube has a thickness of 0.005 inch and the outer shell has a thickness of 0.017 inch. It will be understood that the dimensions given are illustrative but not limiting.

Figure 3:
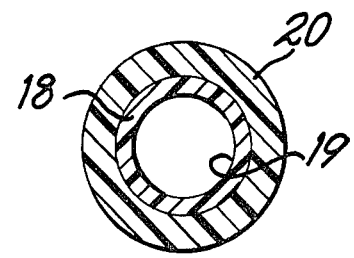
FIG. 3 is an elongated cross-sectional view of tubing having a radiopaque inner core and a transparent outer shell.

Referring to FIG. 3, the thinner inner tube 18 comprises the radiopaque polyurethane composition of Example 1.

The thicker outer wall 20 comprises the following: 65 parts of poly(vinyl chloride) resin plasticized with 34 parts of epoxy plasticizer, Epoxol-9-5, stabilized with 1 part of calcium zinc stabilizer. This multiwall tubing is radiopaque, of low cost construction, because of the P.V.C. heavy wall, and is especially useful in larger sizes for stomach and nasogastric tubes. There is no possibility for PVC or plasticizer to elute into the fluid path (shown as 19 in FIG. 3).

Similar advantages are provided when a tubing is constructed according to these examples, but using nylon, and polypropylene, instead of vinyl in outer wall 20 of FIG. 3.

EXAMPLES 18-19

Figure 4:
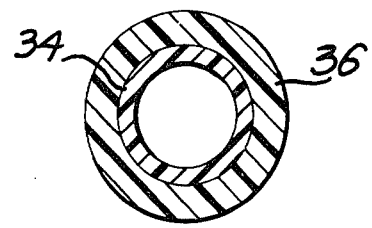
FIG. 4 is an enlarged cross-sectional view of tubing having a transparent core and a radiopaque outer shell.

Two multiwall tubes are made by the procedure of Example 17, except that the inner tube 34 (FIG. 4) comprises, nylon on the one hand, and polypropylene, on the other, and the outer shell 36 comprises the radiopaque thermoplastic polyurethane composition of Example 1. Each tubing provides catheters with superior torque characteristics in terms of resistance to kinking when passed through tortuous body passages.

EXAMPLES 20-21

Two co-tapered multiwall tubes are made by a modification of the procedure in Examples 18-19. The inner and outer layers are extruded concurrently and concentrically through annular concentric orifices of a multi-orifice extruder so as to bond the inner and outer layers together. The co-tapering of the inner and outer layers is obtained by varying the rate of extrusion of the inner and outer layers. See the abovementioned Burlis et al. patent and the co-pending Flynn application. The rate of extrusion of the inner layer gradually varies from a first rate to a second rate while the rate of extrusion of the outer layer gradually varies inversely for the inner layer.

Figure 6:
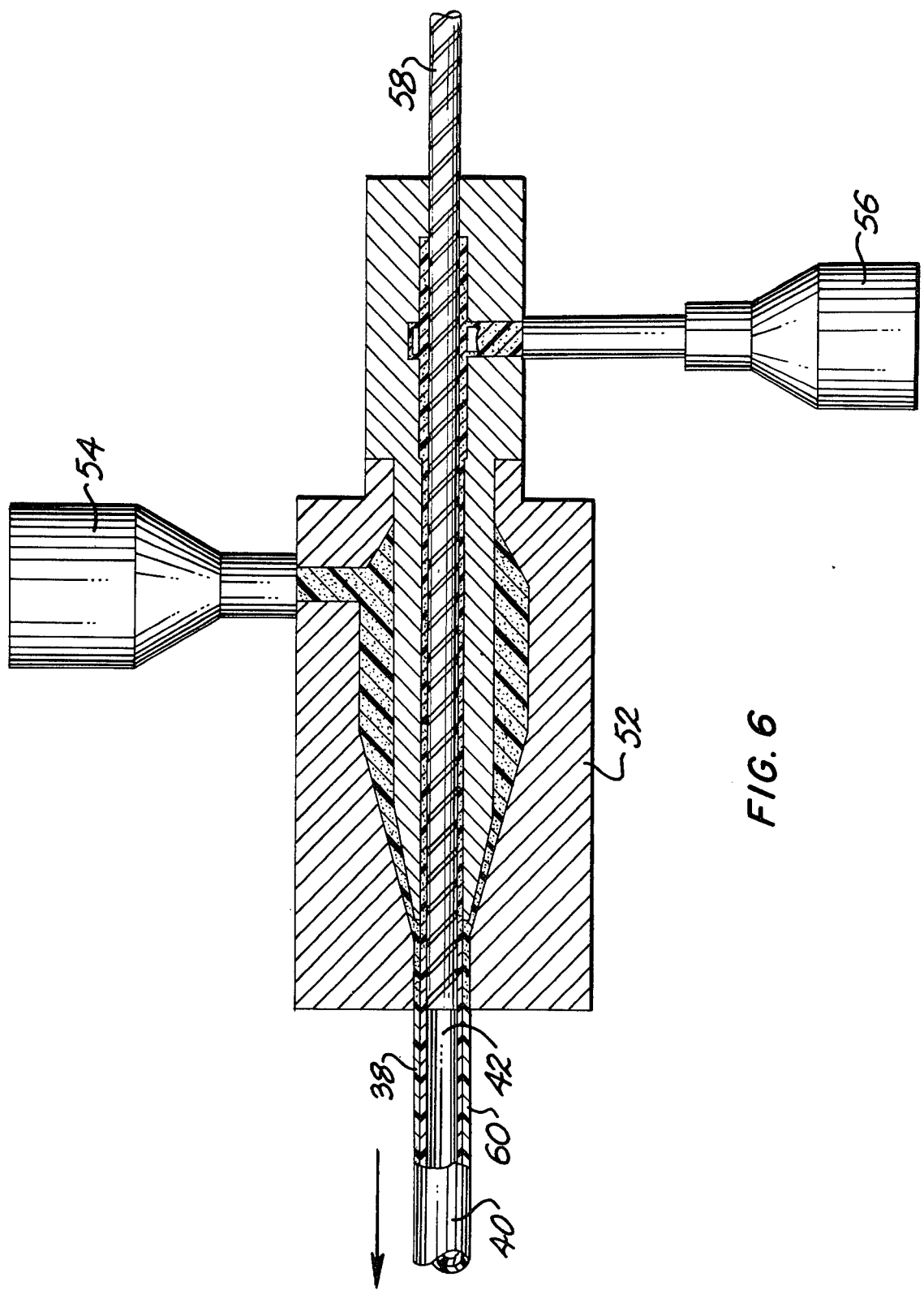

To exemplify further, reference is made to the accompanying drawing of FIG. 6. FIG. 6 is a schematic view of a bi-orifice extrusion head 52 from which tubing 40 is being extruded. Inner layer 60 is being discharged from the inner annular orifice of extrusion head 52. The thermoplastic composition for inner layer 60 is delivered to the extruder head 52 by extruder 56 at a decreasing uniform rate. The outer layer 38 is being discharged from the concentric outer annular orifice of extruder head 52, the thermoplastic composition therefor being supplied by extruder 54 at an increasing rate inversely proportional to the declining rate of extruder 56. Since the tube 40 is being drawn by a Godet (not seen in FIG. 6) the inner layer 60 is tapering downward in thickness while the outer layer 38 is tapering upward in thickness. Air line 58 provides support for the thermoplastic walls 38, 60 and assists in defining lumen 42 during the extrusion. The increasing and decreasing rates of extrusion for inner and outer walls 60, 38 may be provided over any convenient length of time cycle to provide continuous lengths of co-tapered, multi-wall tubing of the invention. The rates of discharge from extruders 54 and 56 may then be reversed to begin the taper in the opposite direction, or the original first cycle may be repeated by synchronizing the speed of extrusion from the two extruders and then again increasing and decreasing the respective rates of discharge from each extruder 54, 56.

Figure 5:
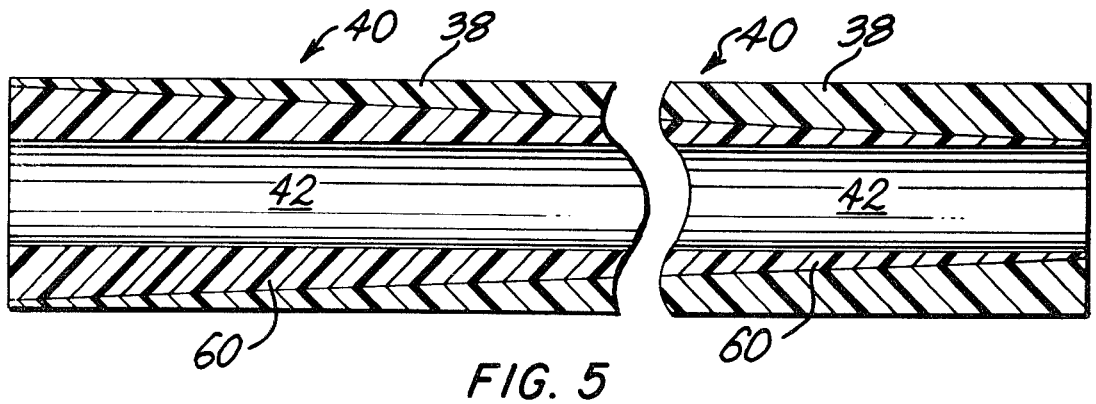
FIG. 5 is an enlarged, fragmentary cross-sectional view along the longitudinal axis of an embodiment tube of this invention having a transparent co-tapered core and a radiopaque, correspondingly co-tapered jacket, extruded as in FIG. 6.

The co-tapered tubings are illustrated in FIG. 5 in one embodiment.

In Example 20, inner wall 60 (FIG. 5) comprises nylon and outer wall 18 comprises the radiopaque thermoplastic polyurethane of Example 1.

In Example 21, inner wall 60 (FIG. 5) comprises polypropylene and outerwall 18 comprises the radiopaque thermoplastic polyurethane of Example 1.

Surgical catheters are formed from the respective tubings of Examples 20 and 21, and they exhibit a degree of flexibility and softening progressively changing from one end to the other. Such medical-surgical catheters have manipulative characteristics which are advantageously employed by the surgical operator in inserting, withdrawing and controlling the catheter.

EXAMPLE 22

A multiwall tube of co-taper construction is made following the preceeding example where the inner core is softer than the outer jacket. This is uniquely advantageous wherein higher torque is desired.

In Example 22, softer inner core 60 (FIG. 5) comprises a 55 to 65D durometer thermoplastic polyurethane containing 20 parts per 100 parts by weight of composition of n-butyl 2,3,4,6-tetraiodobenzoate; and harder outerwall 18 comprises a 75D durometer thermoplastic polyurethane and 20 parts per 100 parts by weight of composition of n-butyl 2,3,4,6-tetraiodobenzoate.

EXAMPLE 23

A thin wall tubing (0.005 wall thickness) is extruded from the following compositions

| Composition | Parts by Weight |
| --- | --- |
| Resin, thermoplastic polyurethane Rucothene 363 | 38.04 |
| Resin, poly(vinyl chloride) BK-80 Goodyear | 10.39 |
| n-Butyl 2,3,4,6-tetraiodobenzoate | 18.39 |
| 2-Ethoxyethyl 2,5-iodobenzoate | 3.08 |
| Epoxy plasticizer, Epoxol 9-5 | 1.21 |
| Stabilizer CZ-11C | 0.17 |
| Bismuth oxychloride | 28.57 |

In comparison with tubing without bismuth oxychloride, this tubing has an enhanced tensile strength and higher radiopacity. The procedure is repeated substituting equal parts by weight of barium sulfate per 100 parts by weight of the composition for the bismuth oxychloride. Again higher tensile strength and higher radiopacity are obtained.

Such tubings are especially useful to provide miniballoon catheters.

Obviously, the compositions of this invention provide tubings with many advantages. With respect to polytetrafluoroethylene catheters, the present invention overcomes an inability to provide a range of soft to hard catheters in a variety of wall thicknesses. This leads to a reduction in mechanical trauma induced by stiffer catheters. Also polytetrafluoroethylene is limited in its ability to accept adequate loading of radiopaque media to be clearly visible, if a small section is lost or fragmented. Furthermore, both the urethanes and the urethane-vinyls can be co-extruded according to this invention with a hard vinyl or urethane liner, which on draw down produces a thin hard knife edge impervious to peel back or fragmentation seen with the polytetrafluoroethylene catheters.

With respect to prior art vinyl tubings, drug vehicle compatibility with the persent tubings is extended in numbers and concentration, and iodine extraction reduced, because of the ability of the urethanes and PVC-urethanes to lock in the indo-esters. For example, they exhibit no spew or exudation when tested for four days at 100% humidity.

Obviously, many variations will suggest themselves to those skilled in this art in light of the above, detailed description. All such obvious variations are within the full intended scope of the appended claims.

I claim:

1. Medical-surgical tubing comprising (a) a resin which includes from 100 to 33 parts by weight of a thermoplastic polyurethane and from 0 to 67 parts of a polymer of a halogenated vinyl monomer; and
(b) a radiopacifier therfor consisting of a diiodobenzoate or a tetraiodobenzoate compound of the formula

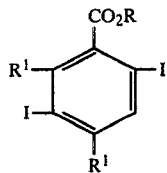

wherein $R^1$ is hydrogen or iodo, and R is alkyl or alkoxyalkyl and a mixture of said compounds, said radiopacifier (b) comprising 10 to 40 parts by weight per 100 parts by weight of (a) and (b).

2. Medical-surgical tubing as defined in claim 1 wherein in said radiopacifier, each $R^1$ is iodo and R is (lower)alkyl or (lower)alkoxy (lower)alkyl.

3. Medical-surgical tubing as defined in claim 1 wherein said radiopacifier is n-butyl 2,3,4,6-tetraiodobenzoate.

4. Medical-surgical tubing as defined in claim 1 wherein compound (b) is 2-ethoxyethyl 2,5-diiodobenzoate.

5. Medical-surgical tubing as defined in claim 1 wherein compound (b) is a mixture of n-butyl 2,3,4,6-tetraiodobenzoate and 2-ethoxyethyl 2,5-diiodobenzoate.

6. Medical-surgical tubing as defined in claim 1 which also includes as a partial replacement for radiopacifier (b) a compound selected from bismuth oxychloride or barium sulfate in an amount sufficient to enhance the radiopacity of said tubing while maintaining its tensile strength.

* * * * *